(12) United States Patent
Ames et al.

(10) Patent No.: US 7,399,784 B2
(45) Date of Patent: Jul. 15, 2008

(54) TOCOPHEROL AND TOCOTRIENOL ANTI-OBESITY MEDICAMENTS

(75) Inventors: Bruce N. Ames, Berkeley, CA (US); Qing Jiang, Berkeley, CA (US)

(73) Assignee: Children's Hospital & Research Center at Oakland, Oakland, CA (US)

(*) Notice: Subject to any disclaimer, the term of this patent is extended or adjusted under 35 U.S.C. 154(b) by 962 days.

(21) Appl. No.: 10/304,918

(22) Filed: Nov. 26, 2002

(65) Prior Publication Data

US 2004/0102385 A1 May 27, 2004

(51) Int. Cl.
*A61K 31/56* (2006.01)
*A61K 31/34* (2006.01)
*A61K 31/35* (2006.01)

(52) U.S. Cl. .................. 514/474; 514/171; 514/458; 514/456; 424/59

(58) Field of Classification Search .................. 424/59; 514/474, 456, 458
See application file for complete search history.

(56) References Cited

U.S. PATENT DOCUMENTS

| | | | |
|---|---|---|---|
| 4,847,071 A | * | 7/1989 | Bissett et al. |
| 5,114,957 A | * | 5/1992 | Hendler et al. ............... 514/356 |
| 5,376,361 A | * | 12/1994 | Perricone ..................... 424/59 |
| 5,849,729 A | * | 12/1998 | Zoumas et al. ............... 514/169 |
| 6,716,451 B1 | * | 4/2004 | Udell et al. .................. 424/455 |

FOREIGN PATENT DOCUMENTS

WO WO 99/34794 * 1/1999

OTHER PUBLICATIONS

Drug Facts and Comparisons, 1997 Edition, pp. 2950-2951.*
Serban, M. G., Lipid Peroxidation in Autoimmune Systemic Vasculitides, Effect of Corticoid Treatment on Lipid Peroxidation, Antioxidant Protection with Vitamin E, Rev. Roum. Med. Int., 32(2):137-142 (1994).*
Serban, M. G., Lipid Peroxidase and Erythrocyte Redox System in Systemic Vasculitides Treated with corticoids. Effect of Vitamin E Administration. 32(4):283-289 (1994).*
"Drug Bank," www.redpoll.pharmacy.ualberta.ca/drugbank.*
"Cortabs," Corticosteroid-Antihistamine Vitamin tablet, www.vetcominc.com.*
Rendina GM., [On the action of prednisone, estrogens, a prednisone-estrogen combination and prednisone-vitamin E in colpokeratosis in ovariectomized rats. (Comparative study)] Aug. 1962;64:501-9. (Abstract only).*

* cited by examiner

*Primary Examiner*—Jennifer Kim
(74) *Attorney, Agent, or Firm*—Richard Aron Osman

(57) ABSTRACT

Anti-obesity compositions include medicaments comprising predetermined amounts of a phytyl substituted chromanol and an obesity-promoting drug, wherein: said medicament is in unit dosage form suitable for pharmaceutical administration; said phytyl substituted chromanol is a gamma-tocopherol, delta-tocopherol, alpha-tocotrienol, gamma-tocotrienol or delta-tocotrienol; said obesity-promoting drug is a corticosteroid or an anti-diabetes drug such as a hypoglycemic drug, starch blocker, glucose production blocker or insulin sensitizer.

1 Claim, No Drawings

TOCOPHEROL AND TOCOTRIENOL ANTI-OBESITY MEDICAMENTS

This invention was made with US Government support under National Institute of Environmental Sciences Center Grant ES01896. The Government has certain rights in this invention.

FIELD OF THE INVENTION

The field of the invention is the use of tocopherols and tocotrienols in anti-obesity medicaments.

BACKGROUND OF THE INVENTION

Vitamin E consists of eight compounds; four tocopherols (alpha-, beta-, gamma-, and delta-) and four tocotrienols (alpha-, beta-, gamma-, and delta-). Among them, only alpha-tocopherol has been extensively studied. Gamma-tocopherol (gamma-T) is the major form of vitamin E in the US diet. However, it has drawn little attention compared with alpha-tocopherol, the primary form of vitamin E found in most supplements. Delta-tocopherol (delta-T) is another form of vitamin E that is rich in some food sources (often found with gamma-T, e.g. in soybeans and soybean oil). Tocotrienols are mainly abundant in palm oil.

Chronic use of a number of medications is known to contribute to obesity. For example, the treatment of diabetes using anti-diabetes drugs, including the thiazolidinedione class (troglitazone, rosiglitazone and proglitazone), commonly leads to weight gain and obesity (Malinowski J M et al, 2000, Clinical Therapeutics, 22, 1151-68). UK Prospective Diabetes Study has clearly demonstrated that weight gain associated with diabetes treatment partially cancels the beneficial effects of tight blood glucose control on cardiovascular events and mortality (UK Prospective Diabetes Study, Group, 1998, Lancet, 352, 854-65). Here we show that tocopherol and tocotrienol compositions can be used to reduce triglyceride accumulation in adipocytes, particularly accumulation resulting from obesity-promoting drug use. Furthermore, the use of combinations of tocopherols or tocotrienols with anti-diabetes drugs provides a superior therapy.

Ismermann et al. 1999, Diabetes Care 22, 1227-1228 report that alpha-tocopherol induces leptin expression in healthy individuals; Ohrvall et al., J Intern Med 1993 Jul;234(1):53-60 report lower tocopherol serum levels in subjects with abdominal adiposity; Sjoholm et al., Biochem Biophys Res Commun 2000 Oct 22;277(2):334-40, report that gamma-tocopherol partially protects insulin-secreting cells against functional inhibition by nitric oxide. U.S. Pat. Nos. 6,239,171 and 5,821,264 appear relevant to this disclosure.

SUMMARY OF THE INVENTION

The invention provides methods and compositions for reducing triglyceride accumulation in adipocytes, particularly accumulation resulting from obesity-promoting drug use. The compositions include medicaments comprising predetermined amounts of a phytyl substituted chromanol and an obesity-promoting drug, wherein: said medicament is in unit dosage form suitable for pharmaceutical administration; said phytyl substituted chromanol is selected from the group consisting of gamma-tocopherol, delta-tocopherol, alpha-tocotrienol, gamma-tocotrienol and delta-tocotrienol.

The phytyl-substituted chromanol is typically isolated or purified to homogeneity or near homogeneity. In particular embodiments, the medicament comprises less alpha-tocopherol than is present in natural Vitamin E compositions, preferably less than 5% alpha-tocopherol, more preferably less than 0.5%, more preferably less than 0.05%. The medicament may comprise various mixtures of gamma- and delta-tocopherol and alpha-, gamma- and delta-tocotrienol.

In particular embodiments, the obesity-promoting drug is a corticosteroid; in other embodiments, the obesity-promoting drug is an anti-diabetes drug such as a hypoglycemic drug, a starch blocker, a glucose production blocker, or an insulin sensitizer.

The invention also provides methods of reducing obesity-promotion, by administering to a patient a subject medicament, as well as methods for reducing triglyceride accumulation in adipocytes by contacting a patient predetermined to have or be predisposed to undesirably high triglyceride accumulation in adipocytes with an effective amount of a phytyl substituted chromanol selected from the group consisting of gamma-tocopherol, delta-tocopherol, alpha-tocotrienol, gamma-tocotrienol and delta-tocotrienol.

DETAILED DESCRIPTION OF PARTICULAR EMBODIMENTS OF THE INVENTION

We disclose that gamma- and delta-T, as well as alpha-, gamma- and delta-tocotrienol, can be used as drugs to reduce triglyceride accumulation in adipocytes. In contrast, alpha-T was much less effective as an anti-obesity agent in our studies. Accordingly, we disclose the use of gamma-T, delta-T, and alpha-tocotrienol, gamma-tocotrienol, and delta-tocotrienol, as well as combinations of these compounds to treat and prevent obesity and/or undesirable weight gain, and their associated diseases including diabetes, cardiovascular diseases and cancers. In addition, these tocopherols and tocotrienols may be given in the form of supplements or neutraceutical drugs or in combination with existing drugs to treat and prevent obesity associated with anti-diabetes and steroid drug therapy.

We have found that tocopherols, particularly gamma-T and delta-T, and tocotrienols, particularly, alpha-, gamma-, and delta-, show dose-dependent anti-adipogenesis activity. The compounds also ameliorate high fat diet-induced obesity and type 2 diabetes in mice. Our data demonstrate that tocopherols and tocotrienols and their combinations can reduce the development of obesity and its associated disorders such as diabetes. Accordingly, our invention provides methods and compositions for inhibiting or reducing triglyceride accumulation in adipocytes, or any manifestation thereof, and/or for reducing the likelihood of developing, and/or for promoting a resistance to undesirable or excess triglyceride accumulation in adipocytes, or any manifestation thereof. The compositions include medicaments comprising predetermined amounts of a phytyl-substituted chromanol and an obesity-promoting drug.

As our methods target triglyceride accumulation in adipocytes and adipogenesis, our methods are applicable to addressing obesity and/or undesirable weight-gain from a wide variety causes, including environmental, pharmaceutical, psychological and behavioral. For example, the invention is generally applicable to the wide variety of drugs known to promote obesity. Well-known examples of obesity-promoting drugs are corticosteroids and anti-diabetes drugs like hypoglycemic drugs, starch blockers, glucose production blockers, and insulin sensitizers. In preferred embodiments, said medicament is in unit dosage form suitable for pharmaceutical administration; and/or said phytyl-substituted chromanol is selected from the group consisting of gamma-T, delta-T, alpha-tocotrienol, gamma-tocotrienol and delta-tocotrienol.

The phytyl-substituted chromanol is typically isolated or purified to homogeneity or near homogeneity. In various embodiments, the chromanol is, prior to admix, purified to at least 80%, preferably at least 90%, more preferably at least 95%, more preferably at least 99% homogeneity. In particular embodiments, the medicament comprises less alpha-T than is present in natural Vitamin E source compositions. In various embodiments, the alpha-T is reduced to less than 50%, preferably less than 20%, more preferably less than 5% of its natural source concentration. In particular embodiments, the pre-admix chromanol/tocopherol is less than 5% alpha-T, more preferably less than 0.5%, more preferably less than 0.05%. The subject medicaments may advantageously include various mixtures of gamma- and delta-T and alpha-, gamma- and delta-tocotrienol, including gamma-T+alpha, gamma and/or delta tocotrienol, delta-T+alpha, gamma and/or delta tocotrienol, and gamma-T+delta-T+alpha, gamma and/or delta tocotrienol.

Exemplary obesity-promoting steroids include prednisone (Deltasone®, Orasone®), methylprednisolone (Medrol®), prednisolone (Prelone®, Pediapred®), dexamethasone (Decadron®), and triamcinolone (Aristocort®). Exemplary obesity-promoting anti-diabetes drugs include hypoglycemic drugs such as glyburide (DiaBeta®, Micronase®), Amaryl®, Glucotrol®, repaglinide (Prandin®), or nateglinide (starlix®); starch blockers such as acarbose (Precose®), and miglitol (Glyset®); glucose production blockers such as metformin (Glucophage®); and insulin sensitizers such as a thiazolindinedion drug such as rosiglitazone (Avandia®) and pioglitazone (Actos®).

The subject medicament components can be purchased commercially and/or prepared from readily available starting materials using conventional methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

The subject medicament compositions may be administered in conjunction with a carrier, vehicle or excipient suitable for use in pharmaceutical compositions. Without being limited thereto, such materials include diluents, binders and adhesives, lubricants, plasticizers, disintegrants, colorants, bulking substances, flavorings, sweeteners and miscellaneous materials such as buffers and adsorbents in order to prepare a particular medicated composition. Such carriers are well known in the pharmaceutical art as are procedures for preparing pharmaceutical compositions.

Depending on the intended route of delivery, the compositions may be administered in one or more dosage form(s) including, without limitation, liquid, solution, suspension, emulsion, tablet, multi-layer tablet, bi-layer tablet, capsule, gelatin capsule, caplet, lozenge, chewable lozenge, bead, powder, granules, dispersible granules, cachets, douche, suppository, cream, topical, inhalant, aerosol inhalant, patch, particle inhalant, implant, depot implant, ingestible, injectable, or infusion. The dosage forms may include a variety of other ingredients, including binders, solvents, bulking agents, plasticizers, etc.

A wide variety of orally administrable compositions may be used. In a particular embodiment, the oral compositions are provided in solid discrete, self-contained dosage units, such as tablets, caplets, lozenges, capsules, gums, etc., which may comprise or be filled with liquid or solid dosages of the recited medicament constituents. A wide variety of dosages may be used, depending on the application and empirical determination; typical dosages range from 1 mg to 1 g, preferably at least 10 mg, more preferably at least 100 mg.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

The above described components are merely representative. Other materials as well as processing techniques and the like are set forth in Part 8 of Remington's Pharmaceutical Sciences, 17th edition, 1985, Mack Publishing Company, Easton, Pa., which is incorporated herein by reference.

The dosage forms of the present invention involve the administration of an active therapeutic substance or multiple active therapeutic substances in a single dose during a 24 hour period of time or multiple doses during a 24 hour period of time. The doses may be uneven in that each dose is different from at least one other dose.

The subject compositions may be administered to effect various forms of release, which include, without limitation, immediate release, extended release, controlled release, timed release, sustained release, delayed release, long acting, pulsatile delivery, etc., using well known procedures and techniques available to the ordinary skilled artisan. A description of representative sustained release materials can be found in the incorporated materials in Remington's Pharmaceutical Sciences.

The subject compositions may be formulated for administration by any route, including without limitation, oral, buccal, sublingual, rectal, parenteral, topical, inhalational, including itnranasal, injectable, including subcutaneous, intravenous, intramuscular, etc., topical, including transdermal, etc. The subject compositions are administered in a pharmaceutically (including therapeutically, prophylactically and diagnostically) effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The following formulation examples illustrate representative pharmaceutical compositions of this invention. The present invention, however, is not limited to the following exemplified pharmaceutical formulations:

Formulation 1—Capsules. Prednisone and gamma-T are blended with a starch diluent in an approximate 1:30:10 weight ratio. The mixture is filled into 200 mg capsules (approx. 5 mg prednisone and 150 mg gamma-T per capsule).

Formulation 2—Capsules. Prednisone and delta-T are blended with a starch diluent in an approximate 1:30:10 weight ratio. The mixture is filled into 200 mg capsules (approx. 5 mg prednisone and 150 mg delta-T per capsule).

Formulation 3—Capsules. Prednisone, gamma-T and gamma-tocotrienol are blended with a starch diluent in an approximate 1:30:30:10 weight ratio. The mixture is filled into 350 mg capsules (approx. 5 mg prednisone, 150 mg gamma-T and 150 mg gamma-tocotrienol per capsule).

Formulation 4—Capsules. Glyburide and gamma-T are blended with a starch diluent in an approximate 1:30:10 weight ratio. The mixture is filled into 200 mg capsules (approx. 5 mg glyburide and 150 mg gamma-T per capsule).

Formulation 5—Capsules. Glyburide and delta-T are blended with a starch diluent in an approximate 1:30:10 weight ratio. The mixture is filled into 200 mg capsules (approx. 5 mg glyburide and 150 mg delta-T per capsule).

Formulation 6—Capsules. Glyburide, gamma-T and gamma-tocotrienol are blended with a starch diluent in an approximate 1:30:30:10 weight ratio. The mixture is filled into 400 mg capsules (approx. 5 mg glyburide, 150 mg gamma-T and 150 mg gamma-tocotrienol per capsule).

Formulation 7—Capsules. Methylprednisolone and gamma-T are blended with a starch diluent in an approximate 1:30:10 weight ratio. The mixture is filled into 200 mg capsules (approx. 5 mg methylprednisolone and 150 mg gamma-T per capsule).

Formulation 8—Capsules. Prednisolone and gamma-T are blended with a starch diluent in an approximate 1:30:10 weight ratio. The mixture is filled into 200 mg capsules (approx. 5 mg prednisolone and 150 mg gamma-T per capsule).

Formulation 9—Capsules. Dexamethasone and gamma-T are blended with a starch diluent in an approximate 1:30:10 weight ratio. The mixture is filled into 200 mg capsules (approx. 5 mg dexamethasone and 150 mg gamma-T per capsule).

Formulation 10—Capsules. Triamcinolone and gamma-T are blended with a starch diluent in an approximate 1:30:10 weight ratio. The mixture is filled into 200 mg capsules (approx. 5 mg triamcinolone and 150 mg gamma-T per capsule).

Formulation 11—Capsules. Amaryl® and gamma-T are blended with a starch diluent in an approximate 1:30:10 weight ratio. The mixture is filled into 200 mg capsules (approx. 5 mg Amaryl® and 150 mg gamma-T per capsule).

Formulation 12—Capsules. Glucotrol® and gamma-T are blended with a starch diluent in an approximate 1:30:10 weight ratio. The mixture is filled into 200 mg capsules (approx. 5 mg Glucotrol® and 150 mg gamma-T per capsule).

Formulation 13—Capsules. Repaglinide and gamma-T are blended with a starch diluent in an approximate 1:30:10 weight ratio. The mixture is filled into 200 mg capsules (approx. 5 mg repaglinide and 150 mg gamma-T per capsule).

Formulation 14—Capsules. Nateglinide and gamma-T are blended with a starch diluent in an approximate 1:30:10 weight ratio. The mixture is filled into 200 mg capsules (approx. 5 mg nateglinide and 150 mg gamma-T per capsule).

Formulation 15—Capsules. Acarbose and gamma-T are blended with a starch diluent in an approximate 1:30:10 weight ratio. The mixture is filled into 200 mg capsules (approx. 5 mg acarbose and 150 mg gamma-T per capsule).

Formulation 16—Capsules. Miglitol and gamma-T are blended with a starch diluent in an approximate 1:30:10 weight ratio. The mixture is filled into 200 mg capsules (approx. 5 mg miglitol and 150 mg gamma-T per capsule).

Formulation 17—Capsules. Metformin and gamma-T are blended with a starch diluent in an approximate 1:30:10 weight ratio. The mixture is filled into 200 mg capsules (approx. 5 mg metformin and 150 mg gamma-T per capsule).

Formulation 18—Capsules. Rosiglitazone and gamma-T are blended with a starch diluent in an approximate 1:30:10 weight ratio. The mixture is filled into 200 mg capsules (approx. 5 mg rosiglitazone and 150 mg gamma-T per capsule).

Formulation 19—Capsules. Pioglitazone and gamma-T are blended with a starch diluent in an approximate 1:30:10 weight ratio. The mixture is filled into 200 mg capsules (approx. 5 mg pioglitazone and 150 mg gamma-T per capsule).

Formulation 20—Liquid. Prednisone (10 mg) and gamma-T are blended (300 mg), sucrose (1.75 g) and xanthan gum (4 mg) are blended, passed through a No. 10 mesh U.S. sieve, and then-mixed with a previously made solution of microcrystalline cellulose and sodium carboxymethyl cellulose (1189, 50 mg) in water. Sodium benzoate (10 mg), flavor, and color are diluted with water and added with stirring. Sufficient water is then added to produce a total volume of 5 mL.

Formulation 21—Liquid. Glyburide (10 mg) and gamma-T are blended (300 mg), sucrose (1.75 g) and xanthan gum (4 mg) are blended, passed through a No. 10 mesh U.S. sieve, and then mixed with a previously made solution of microcrystalline cellulose and sodium carboxyrnethyl cellulose (50 mg) in water. Sodium benzoate (10 mg), flavor, and color are diluted with water and added with stirring. Sufficient water is then added to produce a total volume of 5 mL.

Formulation 22—Liquid. Acarbose (10 mg) and gamma-T are blended (300 mg), sucrose (1.75 g) and xanthan gum (4 mg) are blended, passed through. a No. 10 mesh U.S. sieve, and then mixed with a previously made solution of microcrystalline cellulose and sodium carboxymethyl cellulose (50 mg) in water. Sodium benzoate (10 mg), flavor, and color are diluted with water and added with stirring. Sufficient water is then added to produce a total volume of 5 mL.

Formulation 23—Liquid. Metformin (10 mg) and gamma-T are blended (300 mg), sucrose (1.75 g) and xanthan gum (4 mg) are blended, passed through a No. 10 mesh U.S. sieve, and then mixed with a previously made solution of microcrystalline cellulose and sodium carboxymethyl cellulose (50 mg) in water. Sodium benzoate (10 mg), flavor, and color are diluted with water and added with stirring. Sufficient water is then added to produce a total volume of 5 mL.

Formulation 24—Liquid. Rosiglitazone (10 mg) and gamma-T are blended (300 mg), sucrose (1.75 g) and xanthan gum (4 mg) are blended, passed through a No. 10 mesh U.S. sieve, and then mixed with a previously made solution of microcrystalline cellulose and sodium carboxymethyl cellulose (50 mg) in water. Sodium benzoate (10 mg), flavor, and color are diluted with water and added with stirring. Sufficient water is then added to produce a total volume of 5 mL.

The invention also provides methods of reducing weight gain, obesity, and/or triglyceride accumulation in adipocytes by administering to a patient a subject medicament. In a particular embodiment of this aspect, the invention provides a method for treating a patient with an obesity-related disease such as diabetes, and/or seeking to reduced weight gain, which method comprises administering to said patient a pharmaceutical composition comprising a pharmaceutically acceptable carrier and an effective obesity-related disease/weight-gain-treating amount of a subject medicament. Additionally, this invention is directed to a method for preventing the onset of an obesity-related disease in a patient at risk for developing such disease which method comprises administering to said patient a pharmaceutical composition comprising a pharmaceutically acceptable carrier and an effective obesity-related disease or weight gain -preventing amount of a subject medicament.

This aspect of the invention may be implemented by a first diagnostic step, e.g. determining that the patient is suffering from, subject to, or predisposed to a target disease or condition followed by prescribing and/or administering to the patient a subject medicament, optionally followed by an evaluation/confirmation/prognosis step, e.g. determining an effect of the treatment, such as an amelioration of symptoms of a targeted disease or condition or an indicator thereof. Hence, in one embodiment, the methods additionally comprise the steps of detecting, confirming, and/or determining the presense of or predisposition to obesity, weight gain and/or undesireably high or excessive triglyceride accumulation in adipocytes and/or the step of detecting, confirming and/or determining a resultant reduction of obesity, weight gain and/or triglyceride accumulation in adipocytes The following empirical examples are offered to illustrate this invention and are not to be construed in any way as limiting the scope of this invention.

EMPIRICAL EXAMPLES

I. Gamma-T and delta-T, and tocotrienols, particularly, alpha-, gamma-, and delta-, show dose-dependent anti-adipogenesis activity.

We have found that gamma-T and delta-T, and tocotrienols, particularly, alpha-, gamma-, and delta-, show dose-dependent anti-adipogenesis activity inhibit embryonic cell (C3H10T1/2) differentiation to adipocytes, and decrease intracellular triglyceride accumulation. In contrast, alpa-T was much less effective. For these example, differentiation was induced in the presence of insulin with drugs, including indomethacin, and troglitazone, one of the anti-diabetes drugs of the thiazolidinedione family, as well as 15-deoxy-delta (12, 14)-prostaglandin-$J_2$, a putative endogenous ligand for the peroxisome proliferator-activated receptor-gamma. Our results clearly indicate that tocopherols and tocotrienols inhibit adipogenesis.

II. Gamma-tocopherol, delta-tocopherol, alpha-tocotrienol, gamma-tocotrienol and delta-tocotrienol reduce triglyceride accumulation in adipocytes from a high-fat diet.

We evaluate weight gain and triglyceride accumulation in adipocytes in mice fed a high-fat diet. Six-week-old BALB/c mice are fed powdered chow with various tocopherols and tocotrienols and mixtures thereof, as 0.1%, 3%, 0.02%, or 0.01% food admixtures. For histological analysis of adipose and hepatic tissues and determination of adipocyte size, adipose tissue is removed from each animal and fixed in 10% formaldehyde/PBS and maintained at 4° C. until use. Fixed specimens are dehydrated, embedded in tissue-freezing medium and frozen in dry ice and acetone. White adipose tissue is cut into 10-μm sections, and the sections mounted on silanized slides. The adipose tissue is stained with hematoxylin and eosin (H&E). Mature white adipocytes are identified by their characteristic multilocular appearance. Total adipocyte areas are traced manually and analyzed with Win ROOF software (Mitani Co. Ltd., Chiba, Japan). White adipocyte areas are measured in 400 or more cells per mouse in each group according to methods previously described (Kubota, N. et al.1999, Mol. Cell. 4:597-609).

We find that gamma-tocopherol, delta-tocopherol, alpha-tocotrienol, gammatocotrienol and delta-tocotrienol, and various combinations effectively reduce triglyceride exert antiobesity effects in vivo as measured by reduced weight gain and reduced triglyceride accumulation in adipocytes roughly in proportion to their anti-adipogenetic potencies in vitro. Untreated mice on a high-fat diet gained significantly more weight than the mice on the high-carbohydrate diet. In contrast, treatment with tocopherols and tocotrienols reduce the time-dependent increase in weight on the high-fat diet. Tocopherol and tocotrienols treatments also reduce high-fat diet-induced hyperglycemia and hyperinsulinemia. On the high-fat diet, the glucose-lowering effect of insulin is greater in tocopherol and tocotrienol-treated mice treated than in untreated mice.

III. Formulations 1-3, 7-10 and 20 (supra) reduce triglyceride accumulation in adipocytes in mice fed a low-fat, high-carbohydrate diet and treated with corticosteroids.

We evaluate weight gain and triglyceride accumulation in adipocytes in mice fed a low-fat, high-carbohydrate diet and treated with corticosteroids. Six-week-old BALB/c mice are fed powdered chow with formulations given as 0.1%, 3%, 0.02%, or 0.01% food admixtures. Control animals are identically treated except that the corresponding steroid is provided in tocopherol-stripped corn oil. For histological analysis of adipose and hepatic tissues and determination of adipocyte size, adipose tissue is removed from each animal and fixed in 10% formaldehyde/PBS and maintained at 4° C. until use. Fixed specimens are dehydrated, embedded in tissue-freezing medium and frozen in dry ice and acetone. White adipose tissue is cut into 10-μm sections, and the sections mounted on silanized slides. The adipose tissue is stained with hematoxylin and eosin (H&E). Mature white adipocytes are identified by their characteristic multilocular appearance. Total adipocyte areas are traced manually and analyzed with Win ROOF software (Mitani Co. Ltd., Chiba, Japan). White adipocyte areas are measured in 400 or more cells per mouse in each group according to methods previously described (Kubota, N. et al.1999, Mol. Cell. 4:597-609).

We find that our formulations exert antiobesity effects in vivo as measured by reduced weight gain and reduced triglyceride accumulation in adipocytes roughly in proportion to their anti-adipogenetic potencies in vitro. Control mice treated with corticosteroids alone gained significantly more weight than either the no-treament controls or the formulation-treated mice. Treatment with each tested formulation reduces the time-dependent increase in weight associated with the corresponding corticosteroid.

IV. Formulations 4-6, 11-19 and 21-24 (supra) reduce triglyceride accumulation in adipocytes in mice fed a low-fat, high-carbohydrate diet and treated with anti-diabetic drugs.

We evaluate weight gain and triglyceride accumulation in adipocytes in db/db diabetic mice fed a low-fat, high-carbohydrate diet and treated with various anti-diabetic drugs. Six-week-old mice are fed powdered chow with formulations 4-6, 11-19 and 21-24 given as 0.1%, 3%, 0.02%, or 0.01% food admixtures. Control animals are identically treated except that the corresponding drug is provided in tocopherol-stripped corn oil. For histological analysis of adipose and hepatic tissues and determination of adipocyte size, adipose tissue is removed from each animal and fixed in 10% formaldehyde/PBS and maintained at 4° C. until use. Fixed specimens are dehydrated, embedded in tissue-freezing medium and frozen in dry ice and acetone. White adipose tissue is cut into 10-μm sections, and the sections mounted on silanized slides. The adipose tissue is stained with hematoxylin and eosin (H&E). Mature white adipocytes are identified by their characteristic multilocular appearance. Total adipocyte areas are traced manually and analyzed with Win ROOF software (Mitani Co. Ltd., Chiba, Japan). White adipocyte areas are measured in 400 or more cells per mouse in each group according to methods previously described (Kubota, N. et al.1999, Mol. Cell. 4:597-609).

We find that our formulations exert antiobesity effects in vivo as measured by reduced weight gain and reduced triglyceride accumulation in adipocytes roughly in proportion to their anti-adipogenetic potencies in vitro. Control mice treated with anti-diabetic drugs alone gained significantly more weight than either the no-treament controls or the formulation-treated mice. Treatment with each tested formulation reduces the time-dependent increase in weight associated with the corresponding drug.

V. Formulations 4-6, 11-19 and 21-24 (supra) reduce weight gain in patients with non-insulin-dependent diabetes mellitus (NIDDM).

For these experimental protocols, we adapted the methods of DeFronzo, et al., N Engl J Med 1995 Aug 31;333(9):541-9, to perform randomized, parallel-group, double-blind, controlled studies in which Formulations 1-24, the corresponding anti-diabetic drugs alone, or placebos are given for 29 weeks to moderately obese patients with NIDDM whose diabetes was inadequately controlled by diet. In addition to weight gain, plasma glucose, lactate, lipids, insulin, and glycosylated hemoglobin are evaluated before, during, and at the end of the study. At the end of the study patients in the treatment groups, as compared with patients in the placebo group, have lower mean (+/− SE) fasting plasma glucose concentrations and glycosylated hemoglobin values. The effect of the fomulation treatments alone is similar to that of anti-diabetic drugs alone. Treatment groups have decreases in plasma total and low-density lipoprotein cholesterol and triglyceride concentrations, whereas the values in the respective control groups are unchanged. No significant changes are observed in fasting plasma lactate concentrations in any of the groups. No significant weight gain is observed in either the control or formulation treatment groups, whereas anti-diabetic drug treatment groups present significant weight gain.

The foregoing descriptions of particular embodiments and examples are offered by way of illustration and not by way of limitation. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

All publications and patent applications cited in this specification and all references cited therein are herein incorporated by reference as if each individual publication or patent application or reference were specifically and individually indicated to be incorporated by reference. Any material accompanying this application on compact disc or other recorded medium is incorporated by reference.

What is claimed is:

1. An orally administrable medicament comprising predetermined amounts of a phytyl substituted chromanol and an obesity-promoting drug, wherein:
    said medicament is in unit dosage from selected from the group consisting of tablets, caplets, lozenges, capsules, gums and pills;
    said phytyl substituted chromanol is selected from the group consisting of gamma-tocopherol, delta-tocopherol, alpha-tocotrienol, gamma-tocotrienol and delta-tocotrienol;
    said obesity-promoting drug is a corticosteroid;
    wherein the phytyl substituted chromanol is less than 5% alpha-tocopherol; and
    wherein the phytyl substituted chromanol is purified to at least 95% homogeneity.

* * * * *